US006861224B2

United States Patent
Fujita et al.

(10) Patent No.: US 6,861,224 B2
(45) Date of Patent: Mar. 1, 2005

(54) PROTEIN DETECTING DEVICE

(75) Inventors: Shozo Fujita, Kawasaki (JP);
Shunsaku Takeishi, Kawasaki (JP);
Tsuyoshi Fujihara, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 94 days.

(21) Appl. No.: 10/284,094

(22) Filed: Oct. 31, 2002

(65) Prior Publication Data

US 2003/0087296 A1 May 8, 2003

(30) Foreign Application Priority Data

| Nov. 2, 2001 | (JP) | 2001-338318 |
| Mar. 25, 2002 | (JP) | 2002-083991 |
| Mar. 29, 2002 | (JP) | 2002-096165 |

(51) Int. Cl.$^7$ .............................................. C12Q 1/68
(52) U.S. Cl. ........................................................ 435/6
(58) Field of Search ............................... 436/518, 91.6; 536/25.3, 23.1; 204/400

(56) References Cited

PUBLICATIONS

Elizabeth M. Boon et al.; Nature Biotechnology, vol. 18, pp. 1096–1100, Oct. 2000.
Gerhard Hartwich et al.; J. American Chemical Society, vol. 121, No. 46, pp. 10803–10812, 1999.

*Primary Examiner*—Kenneth R. Horlick
*Assistant Examiner*—Heather G. Calamita
(74) *Attorney, Agent, or Firm*—Armstrong, Kratz, Quintos, Hanson, & Brooks, LLP

(57) ABSTRACT

A protein detecting device, which comprises: (1) a detecting unit having a bonding section, which has properties for specifically bonding to a protein to be detected, a detecting section for detecting the bonding of the protein to be detected to the bonding section, the detecting section being made up of a polynucleotide double strand and a charge separating group, and an electrode section detecting the change in electrical conductivity of, or amount of transferred charge in, the polynucleotide double strand modified by the bond of the protein, (2) a standard electrode, (3) a reference electrode, (4) a container for housing the detecting unit, the standard electrode and the reference electrode, and containing a sample solutions comprising the protein to be detected, and (5) a measuring unit for measuring the protein based on a signal detected in the detecting unit.

11 Claims, 13 Drawing Sheets

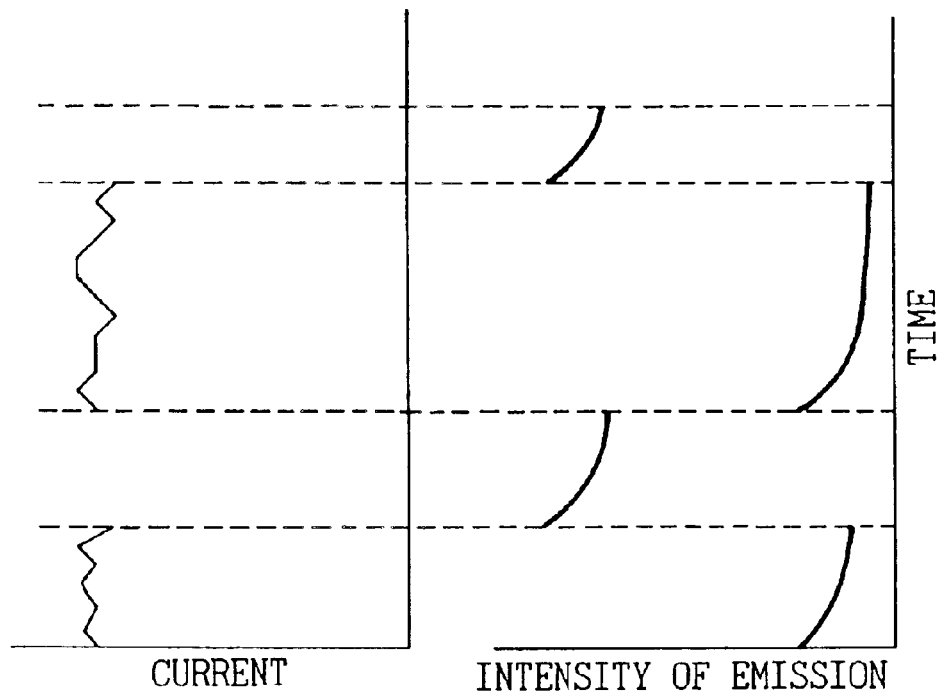
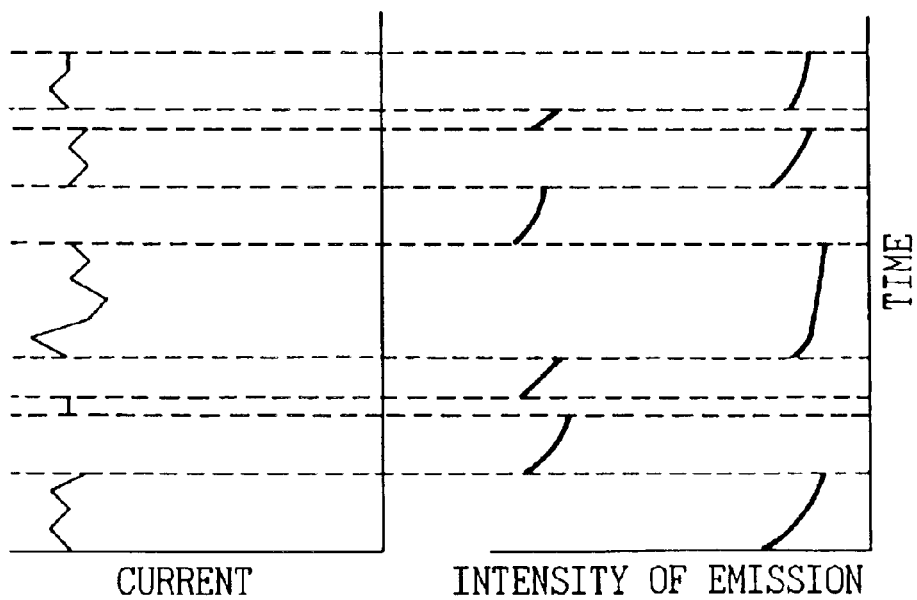

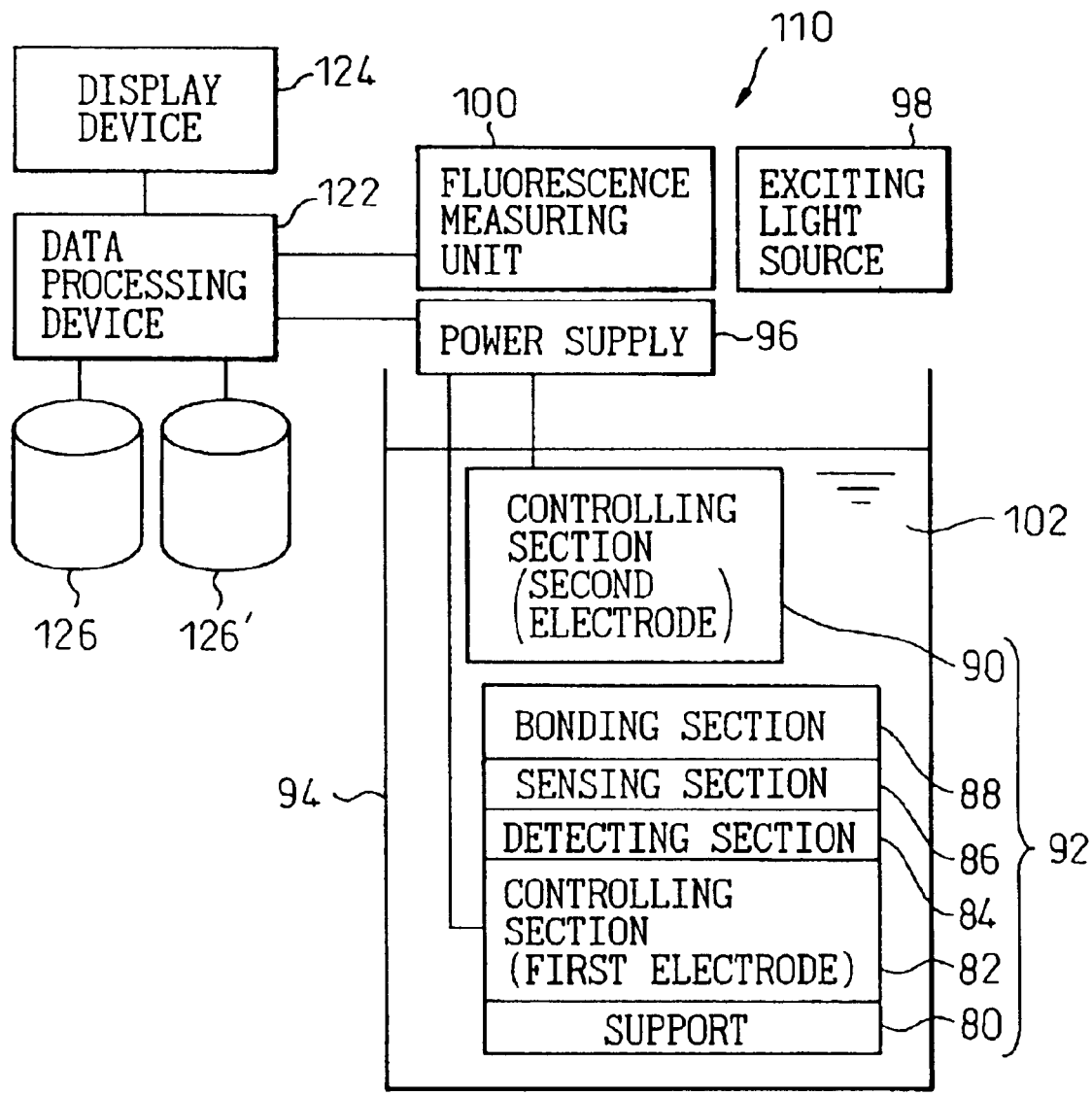

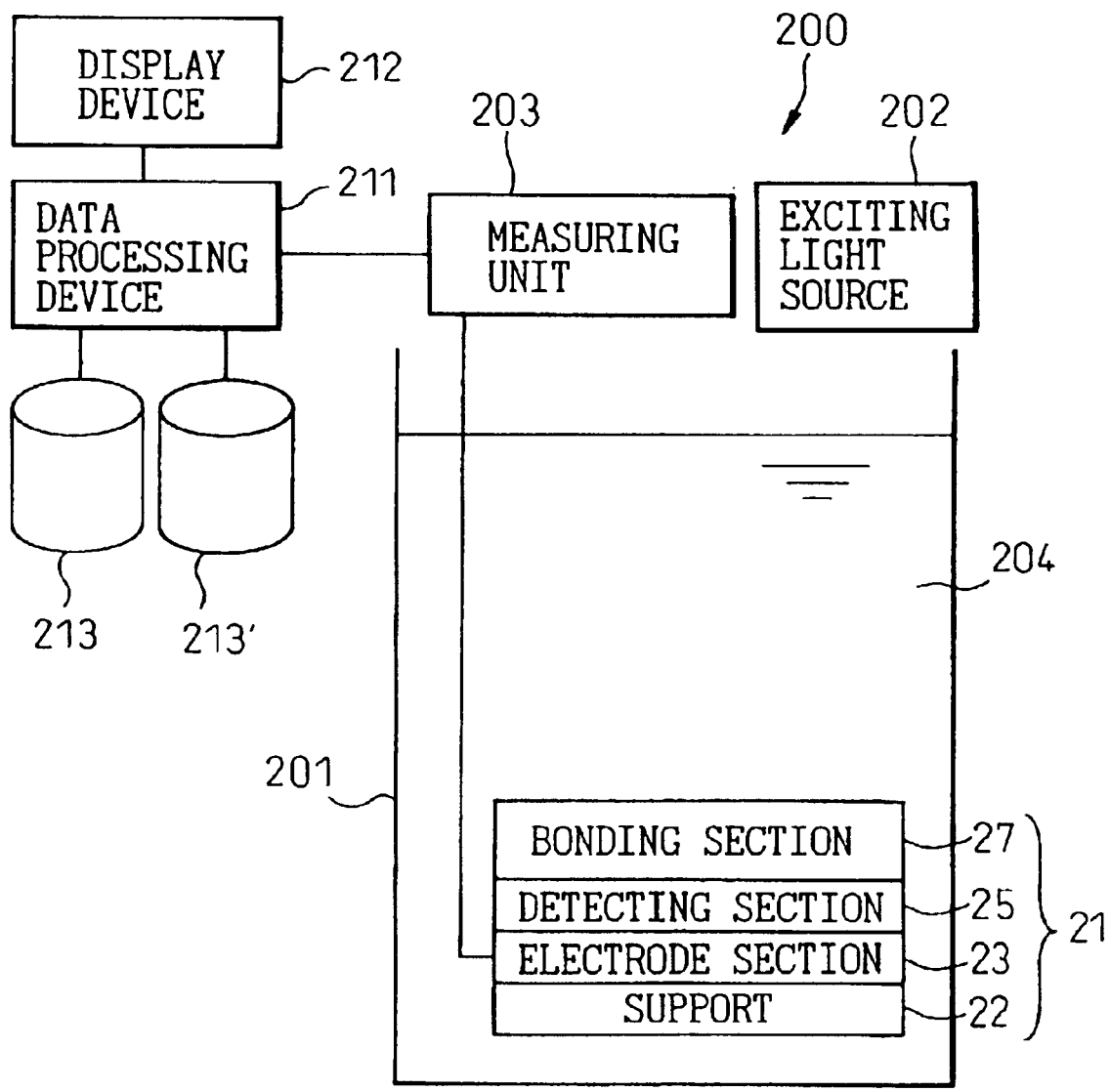

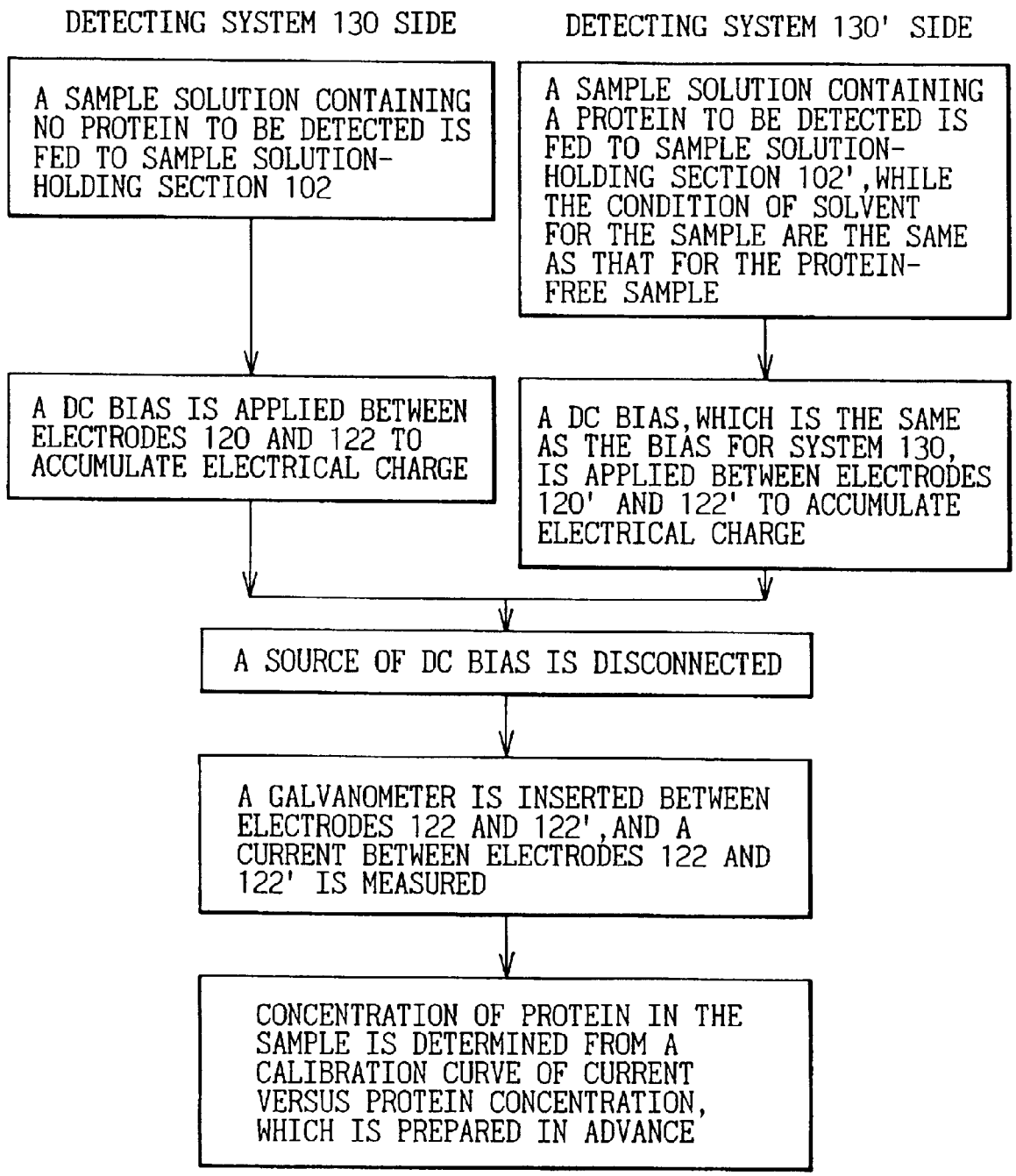

PROTEIN DETECTING DEVICE

CROSS-REFERENCE TO RELATED APPLICATIONS

This application is based upon and claims the priority of Japanese Patent Application Nos. 2001-338318, filed on Nov. 2, 2001; 2002-83991, filed on Mar. 25, 2002; and 2002-96165, filed on Mar. 29, 2002, the contents thereof being incorporated herein by reference.

BACKGROUND OF THE INVENTION

1. Field of the Invention

The invention relates to a device for detecting/determining a protein or proteins and, more specifically, to a device capable of the detection/determination of a protein or proteins without labeling them.

2. Description of the Related Art

The human genome project, developed in 1990s, was an attempt for some countries to share decoding of all of the human genetic code. It has been announced that a draft was finished in the summer of 2000. It is expected that, as functional genome science and structural genome science progress after this, it will be revealed what function each of the decoded human genome sequence data pertains to.

The human genome project has brought a large change in paradigm to scientific technology and industries involving life sciences. For example, diabetes mellitus has been classified based on symptom of high blood sugar level and, with respect to the cause of onset, has been classified, based on a level of capacity of producing insulin in a patient's body, into type I (insulin cannot be produced in the body) and type II (the amount of insulin cannot be controlled in the body). The human genome project presented all the data of amino-acid sequence of proteins, such as enzymes and receptors, pertaining to the control of the detection of blood glucose and insulin, or synthesis, decomposition and the like of insulin, and a DNA sequence of genes pertaining to the control of the amounts of such proteins exists. Using such data, diabetes mellitus, a phenomenon of the control of blood glucose level being not functioned, can be classified into subtypes, depending on what proteins pertaining to the process of the synthesis, decomposition and the like of insulin are upset, and, accordingly, it must become possible to carry out an appropriate diagnosis and cure. Particularly, development of new drugs based on the genome data, in which drugs are developed for particular proteins based on the human genome sequence, is being energetically promoted by the pharmaceutical industry, and it is expected that the relief and cure of a symptom will be effected by understanding the conditions of a sequence of proteins which are functionally related to each other for the symptom and by administering a genetically developed drug.

To make this possible, a technique enabling simple measurement of the amounts of a sequence of proteins, which are functionally related to each other, is needed. However, such a technique is being developed as a technique of analyzing proteome. As a currently established method, there is known a method in which measurement is carried out by combining two-dimensional electrophoresis and mass spectrometric analysis, which requires a relatively large-scale apparatus. To determine a patient's symptoms at a clinical site, such as a laboratory or at the bedside in a hospital, the development of a simple, novel technique is needed.

A so-called DNA chip is designed to be adapted for the determination of a DNA in a sample to be detected by previously introducing thereinto a fluorescent pigment during the amplification (increment) thereof by a PCR (polymerase chain reaction), and determining the amount of DNA bonded to complementary DNA chains arranged on a chip in the form of array by the intensity of fluorescence. In contrast, proteins cannot be processed by what corresponds to amplification by the PCR reaction, as in the case of DNA. Also, there has been a problem that when plural kinds of proteins are mixed and present in a sample, uniformly introducing a fluorescence label into them cannot be used because the reactivities between the fluorescent pigment and the individual proteins are different.

SUMMARY OF THE INVENTION

It is an object of the invention to provide a device enabling specific determination of a biopolymer or biopolymers, such as proteins, without providing the biopolymer or biopolymers to be detected with a fluorescence label or the like.

It is also an object of the invention to provide a technique, which serves as a constituent technique applicable to a so-called array-chip technology, for obtaining data useful in the point of view of proteome perceiving biopolymers as a mass.

In short, according to the invention, plural kinds of proteins in a sample are detected and determined together by arranging, in a form of array, antibodies or derivatives thereof having an affinity to a protein to be detected, and based on correspondences between signals generated by the bond of the proteins to them and the location thereof in the array.

The protein detecting device according to a first aspect of the invention comprises: (1) a detecting unit having a bonding section, which has properties for specifically bonding to a protein to be detected, a detecting section for detecting the bonding of the protein to be detected to the bonding section, the detecting section being made up of a polynucleotide double strand and a charge separating group, and an electrode section picking up the change in electrical conductivity of or amount of transferred charge in the polynucleotide double strand modified by the bond of the protein, (2) a standard electrode, (3) a reference electrode, (4) a container for housing the detecting unit, the standard electrode and the reference electrode, and containing a sample solutions comprising the protein to be detected, and (5) a measuring unit for measuring the protein based on a signal detected in the detecting unit.

The protein detecting device according to a second aspect of the invention comprises: (1) a detecting unit having a bonding section, which has properties for specifically bonding to a protein to be detected, a sensing section made up of a polynucleotide double strand and a fluorescent pigment group, a detecting section for detecting the bonding of the protein to be detected to the bonding section, the detecting section being made up of a quenching pigment group, and a controlling section for setting the conformation of the sensing section at an initial state, the controlling unit being made up of a pair of electrodes, (2) a container for housing the detecting unit, and containing a sample solution comprising the protein to be detected, (3) an electric power supply connected to the electrodes of the controlling section, (4) a source of exciting light for exciting the fluorescent pigment group in the sensing section to generate fluorescence, and (5) a unit for measuring the fluorescence.

The protein detecting device according to a third aspect of the invention comprises: (1) a detecting unit having a bonding section, which has properties for specifically bonding to a protein to be detected, a detecting section for detecting the bonding of the protein to be detected to the bonding section, the detecting section being made up of a polynucleotide double strand and a light emitting group, and an electrode section to the surface of which the detection section is anchored, (2) a container for housing the detecting unit, and containing a sample solutions comprising the protein to be detected, and (3) a unit for measuring emitted light.

In another aspect, the invention provides a biopolymer detecting device comprising one or more pairs of electrodes provided with a member (detecting member) having a site (bonding site) capable of being bonded to a biopolymer to be detected, and generating an electrical signal as a detection signal for the biopolymer, a sample solution-holding section for holding a sample solution containing the biopolymer to be detected between the electrodes, and an electrical circuit for processing the electrical signal from the electrode.

The biopolymer detecting device of this aspect detects and determines the biopolymer to be detected, based on the difference in electrical signal from the electrode before and after filling the sample holding section with the sample solution, which difference is caused by the biopolymer to be detected being bonded to the bonding site which the detecting member on the electrode has. For the detection/determination, a calibration curve, which has been previously prepared, is used. The detection/determination of the biopolymer is possible even when only one pair of electrodes is used. In the case of a plurality of pairs of electrodes, more precise detection/determination is possible.

BRIEF DESCRIPTION OF THE DRAWINGS

The above and other objects and advantages of the invention will be well understood and appreciated by a person with ordinary skill in the art, from consideration of the following detailed description made by referring to the attached drawings, wherein:

FIG. 13 shows a flow chart indicating the procedure for the determination of a protein to be detected.

DETAILED DESCRIPTION OF THE INVENTION

Figure 1A:
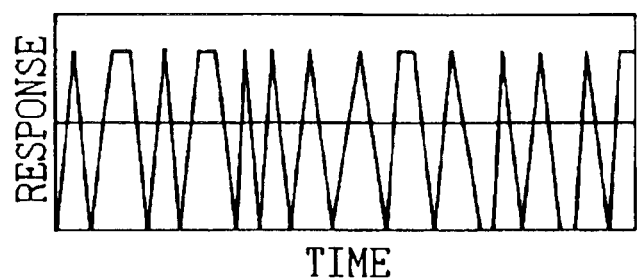
FIG. 1A schematically shows a response observed as electrical conduction through a polynucleotide double strand relative to time in the case where a protein to be detected is not bonded to a bonding section at the end of the polynucleotide double strand, FIG. 1B schematically shows a response observed as electrical conduction through a polynucleotide double strand relative to time in the case where a protein to be detected is bonded to a bonding section at the end of the polynucleotide double strand, FIG. 2A schematically shows a response observed as the reduction of intensity of fluorescence emitted by a fluorescent pigment present at one end of a polynucleotide double strand relative to time in the case where a protein to be detected is not bonded to a bonding section at the end of the polynucleotide double strand, FIG. 2B schematically shows a response observed as the reduction of intensity of fluorescence emitted by a fluorescent pigment present at one end of a polynucleotide double strand relative to time in the case where a protein to be detected is bonded to a bonding section at the end of the polynucleotide double strand, FIG. 3A schematically shows the intensity of emission from a light emitting group and the amount of current running from the light emitting group to an electrode through a polynucleotide in the case where an objective protein is not captured, FIG. 3B schematically shows the intensity of emission by a light emitting group and the amount of current running from the light emitting group to an electrode through a polynucleotide in the case where an objective protein is captured, FIG. 4 schematically illustrates a detecting unit used in protein detecting devices according to the first and third aspects of the invention, FIG. 5 schematically illustrates the entire construction of a measuring apparatus using the protein detecting device of Example 1, FIG. 6 schematically illustrates a detecting unit used in the protein detecting device of Example 2, FIG. 7 schematically illustrates the entire construction of a measuring apparatus using the device comprising the detecting unit shown in FIG. 6, FIG. 8 schematically illustrates a measuring apparatus using the protein detecting device of Example 3.

The detecting unit in the protein detecting device according to the invention corresponds to a so-called protein chip, and is designed to detect, for example, the decline or enhance of part of a series of protein interaction network function starting from insulin receptor and ending with glycogen catabolic enzyme in the case where hepatocyte having diabetes changes intracellular metabolism of glycogen dependent on a state of insulin acceptance. By the use of this technique, it becomes possible to know the population of proteins, including a so-called posttranslational modification such as a phosphorylation or an addition of a sugar chain. Consequently, instead of detecting diabetes mellitus on the basis of symptom as before, it becomes possible to know that the decline in function of a certain protein pertaining to the interaction network causes incompetence of glucose metabolism, and appropriate diagnosis and cure corresponding to the cause of dysfunction, as well as verification of a therapeutic result, become possible.

Of course, a similar technique is applicable to the entirety of multifactorial disease, such as hypertension, hyperlipidemia, cancer (incompetence of control of cell proliferation) or the like, in addition to diabetes mellitus.

The protein detecting device according to the first aspect of the invention uses, as the protein detecting unit, a unit having a bonding section, which has properties for specifically bonding to a protein to be detected, a detecting section for detecting the bonding of the protein to be measured to the bonding section, the detecting section being made up of a polynucleotide double strand and a charge separating group, and an electrode section picking up the change in electrical conductivity of, or amount of transferred charge in, the polynucleotide double strand modified by the bond of the protein.

The bonding section in this detecting unit is made up of an antibody which specifically bonds to a protein to be detected, or to a fragment of such an antibody obtained by limitedly decomposing the antibody by, for example, a protease, or an organic compound or biopolymer having an affinity to a protein to be detected. As the antibody, a monoclonal immunoglobulin IgG antibody can be used, for example. Also, as a fragment derived from an IgG antibody, a Fab fragment of an IgG antibody can be used, for example. In addition, a piece derived from such a Fab fragment can be also used. Examples of organic compounds having an affinity to a protein to be measured include enzyme substrate analogues, such as adenosine-5'-O-(3-thiotriphosphate) (also called ATP-gamma-S), enzyme activity inhibitors, neurotransmission inhibitors (antagonists) and the like. As examples of biopolymers having an affinity to a protein to be detected, proteins representing substrates or catalysts for the protein to be detected, elementary proteins forming a molecular complex with the protein to be detected, can be enumerated. In the case where a substance, such as one described above, forming the bonding section cannot be directly linked and fixed to a polynucleotide double strand forming the detecting section, it may be fixed through a linking moiety (typically a divalent group) useful for the linkage.

The detecting section is formed as a nano-structure made up of a polynucleotide double strand and a charge separating group. One end of the polynucleotide double strand is linked to the bonding section as described above, and the other end is connected to an electrode described later. The charge separating group may be added to the polynucleotide double strand by covalent bonding, or may be contained within the structure of the polynucleotide double strand (interposition between adjacent complementary moieties (intercalation)), or may be incorporated within a nucleotide chain forming the polynucleotide double strand by replacing a part thereof. The charge separating group is preferably present in the vicinity of the opposite end of the electrode, i.e., the end of the polynucleotide double strand for the bonding section.

A polynucleotide double strand has electrical conductivity in the longitudinal direction of the strand due to a pi-electron stack of aromatic rings of bases forming nucleotides. On the other hand, a charge separating group in the invention combined with such a polynucleotide double strand is a group causing charge separation when subjected to action of a potential difference, excited light, or the like, and may be a compound when contained within a polynucleotide double strand as described above. Specifically, the charge separating group is a group which is subjected to withdrawal of electron by a reagent (charge acceptor, e.g., a ferrocyanide ion referred to below) in a sample solution to generate a positive hole, a group generating an electron and a positive hole by light excitation, or the like. Either of the electron or the hole generated from a charge separating group by the charge separation contributes to electrical conduction through the polynucleotide double strand, which can be detected by an electrode connected to one end of the polynucleotide double strand. In other words, in the invention, electrical conductivity through the polynucleotide double strand is detected in the state in which the charge separating group is caused to be charge-separated. As the charge separating group, porphyrin ferrocenated or the like can be used.

When an electron and a hole are generated from a charge separating group, as in the case of the use of light excitation, the electron or the hole not pertaining to the electrical conduction through a polynucleotide double strand is received by a charge acceptor present in a sample solution. As the charge acceptor, an anion, such as ferrocyanide ion, can be used. When such an anion $M^{m-}$ is used, and the anion after receiving a charge is represented by $M^{n-}$, m is smaller than n in the case of the anion receiving an electron, and m is larger than n in the case of the anion receiving a hole. When a cation is used as the charge acceptor, there is an opposite relationship.

In the invention, the change in the charge transfer state of the polynucleotide double strand modified by the bond of a protein to the bonding section at one end of the polynucleotide double strand, i.e., the change in the electrical conductivity or the amount of transferred change, is detected by the electrode to which the other end of the double strand is connected. The electrical conductivity developed along the direction of longitudinal axis of the polynucleotide double strand at the state at which the charge separating group in the detecting section is caused to be charge-separated depends on the pi-electron stack of aromatic rings of the bases forming nucleotides. The polynucleotide double strand loses electrical conductivity when the pi-electron stack temporarily loses its balance due to its molecular motion (fluctuation of the molecular structure). When a particular protein is bonded to the bonding section located at the end of a detecting unit, this molecular motion is subjected to the action of the mass of the protein, and becomes slower relative to the case where the protein is not bonded.

Figure 1B:
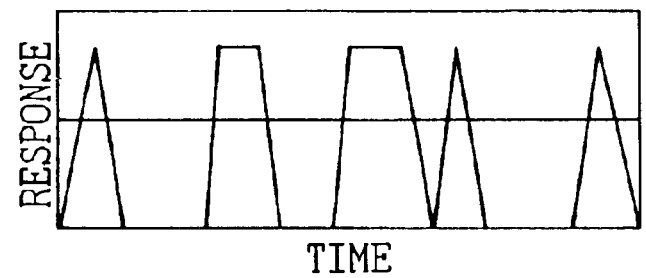

By way of example, electrical conductivities through a polynucleotide double strand in the cases of no protein is bonded and a protein is bonded are detected as responses with time as schematically shown in FIGS. 1A and 1B, respectively, because the molecular motion is more vigorous in the former case, and is slower in the latter case.

The effect of loss of electrical conductivity of the polynucleotide double strand structure may be larger by enhancing the fluctuation of the double strand by purposely introducing a crack in the polynucleotide double strand structure by, for example, providing discontinuity at one or more locations somewhere along one nucleotide chain of the double strand. To provide the nucleotide chain with discontinuity, it is useful to cut out part of a phosphate residue linking adjacent nucleotides to each other. Alternatively, a structure containing a nucleotide chain having a discontinuity can be also obtained by combining one nucleotide chain with one or more short nucleotide chains, which have only part of a sequence complementary to the sequence of the former nucleotide chain, to thereby spontaneously provide a polynucleotide double strand.

The electrode for picking up the change in electrical conductivity of or amount of transferred charge in a polynucleotide double strand modified by the bond of a protein is made from a material which is stable in a sample solution. For the detection/determination of plural kinds of proteins, an electrode is provided for each of the proteins, and one end of a polynucleotide double strand of the detecting section is connected to each of the electrodes, with the detecting section being connected to, at the other end, the bonding section formed of an antibody for each of the proteins.

The connection of the polynucleotide double strand to the electrode can be effected by linking a mercapto group introduced to one end of one nucleotide chain to the electrode through a spacer ($-(CH_2)_n-$ or the like is typically used). The polynucleotide double strand structure thus connected to the electrode nearly linearly extends at a nearly constant angle to the surface of the electrode.

As components other than the detecting unit composing the protein detecting device of the invention, i.e., the standard electrode, reference electrode, sample container and measuring unit, those used for the measurement of a conductivity of a substance in a sample solution can be used.

The protein detecting device according to the second aspect of the invention will now be described. This device uses, as the protein detecting unit, a unit having a bonding section, which has properties for specifically bonding to a protein to be detected, a sensing section made up of a polynucleotide double strand and a fluorescent pigment group, a detecting section for detecting the bonding of the protein to be detected to the bonding section, the detecting section being made up of a quenching pigment group, and a controlling section for setting the conformation of the sensing section at an initial state, the controlling unit being made up of a pair of electrodes.

The bonding section in this detecting unit may be similar to the bonding section used in the detecting unit of the device of the first aspect of the invention.

The sensing section is formed as a nano-structure made up of a polynucleotide double strand and a fluorescent pigment group. One end of the polynucleotide double strand is linked to the bonding section as described above, and the other end is connected to one of a pair of electrodes in the controlling section described later. The fluorescent pigment group may be added to the polynucleotide double strand by covalent bonding, or may be contained within the structure of the polynucleotide double strand (insertion between adjacent complementary moieties (intercalation)), or may be incorporated within a nucleotide chain by replacing part thereof. The fluorescent pigment group is designed to be present at the vicinity of the end of the polynucleotide double strand for the bonding section.

The fluorescent pigment group is selected from substances which are excited by light to generate fluorescence. Examples of the fluorescent pigment groups which can be preferably used in the invention include fluorescein maleimide, Cy3 (trade mark) and the like.

The detecting section is made up of a quenching pigment group for detecting the bond of a protein to be detected to the bonding section, and the quenching pigment group is fixed to any support. In general, the quenching pigment group is fixed to an electrode, to which the sensing section as described above is linked, of a pair of electrodes in the controlling section described below.

The quenching pigment group is selected from those causing effective optical quenching for a fluorescent pigment group used. For example, when fluorescein maleimide or Cy3 (trade mark) is used as the fluorescent pigment group, D-damine B sulfonyl chloride or Cy5 (trade mark) can be used, respectively. More preferably, a combination of a fluorescent pigment group and a quenching pigment group, which provides a FRET (fluorescence resonance energy transfer) effect, is used.

The controlling section is made up of a pair of electrodes. One of the electrodes (a first electrode) is connected to one end, which is not connected to the bonding section, of the polynucleotide double strand forming the sensing section, and the other (a second electrode) is positioned separately from the bonding section, sensing section and detecting section.

It is known that when one end of the polynucleotide double strand is fixed to a first electrode, this electrode is immersed together with a second electrode in an aqueous solution, and an electric field, e.g., an alternating electric field, is applied to between these electrodes, the polynucleotide double strand is linearly elongated in the direction of the electric field, and, when the electric field is eliminated, the strand is spontaneously flocculated. The protein detecting device of the invention utilizes this property of polynucleotide double strand, to thereby detect whether or not a protein to be detected is bonded to an antibody fixed to the end on the polynucleotide double strand.

When the detecting unit composed as described above is placed in a sample solution containing a protein to be detected, and an electric field is applied between the electrodes of the controlling section, the double strand will be in a state of the elongation in the direction of the electric field (initial state), as described above. When the detecting unit in this state is irradiated with appropriate light from an exciting source, the fluorescent pigment group is excited and generates fluorescence. Thereafter, by removing the electric field, the double bond, which has been elongated, is flocculated. At this time, as the end of the double strand structure of the sensing section, opposed to the end thereof having the fluorescent pigment group bonded, is connected to the electrode to which the quenching pigment groups are fixed, the fluorescent pigment group is relatively close to the quenching pigment group and, consequently, a decrease in the intensity of fluorescence is observed. When the electric field is applied again, the double strand is elongated and, accordingly, the bonding section regains the linearly elongated conformation at the initial state. It is also possible to designate the conformation of flocculated double strand structure for the initial state. In this case, the intensity of fluorescence is decreased in the initial state, and the double strand structure is elongated by the application of electric field, resulting in the increase in the intensity of fluorescence.

When a protein to be detected is present in a sample solution, the protein is bonded to an antibody at the bonding section. As a result, the mass of the end of the double strand structure is increased and, citing an example of the double strand structure elongated at the initial state, a time required to complete the spontaneous flocculation after the removal of electric field, i.e., a time taken for the intensity of fluorescence to be reduced to a certain level, is increased, leading to the variation in a time constant. Accordingly, by detecting the difference in time constant during the increase or decrease in the intensity of fluorescence at the initial state to a certain level, it can be detected whether or not a protein is bonded to the bonding section. An extent to which the time is increased (or decreased) is varied depending on the amount of protein present in a sample solution, so that, by knowing the extent, the amount of protein in the sample solution can be determined, and the type of protein can be identified depending on from what double strand, among an array of double strands, the signal comes.

Figure 2A:
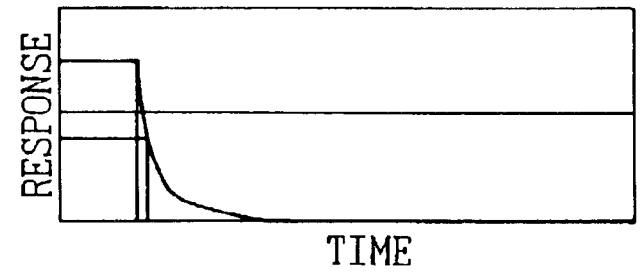
Figure 2B:
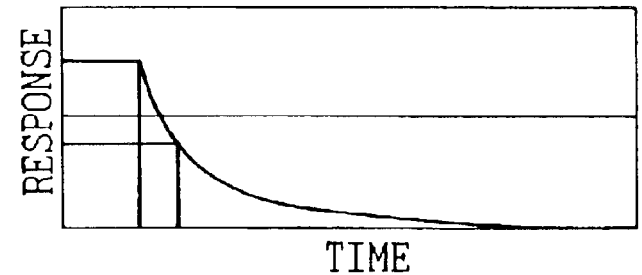

By way of example, respective responses observed as the decrease in the intensity of fluorescence in the cases of a protein bonded to and not bonded to the bonding section are schematically shown in FIGS. 2A and 2B.

As components other than the detecting unit composing the protein detecting device of the invention, i.e., the container for a sample solution, electric power supply, source of exciting light, and unit for measuring fluorescence, those commonly available can be used.

The protein detecting device according to the third aspect of the invention will now be described. This device uses, as the protein detecting unit, a unit having a bonding section, which has properties for specifically bonding to a protein to be detected, a detecting section for detecting the bonding of the protein to be detected to the bonding section, the detecting section being made up of a polynucleotide double strand and a light emitting group, and an electrode section to receive exciting electrons from the light emitting group for the quenching of the light emitting group excited by light.

The bonding section in this detecting unit may be similar to the bonding section of the detecting unit used in the device of the first aspect as earlier described.

The detecting section is formed as a nano-structure made up of a polynucleotide double strand and a light emitting group. As in the detecting unit of the first aspect, one end of the polynucleotide double strand is connected to the bonding section, and another end is connected to the electrode section.

As the light emitting group, a substance which is excited by irradiated exciting light and, in turn, emits light is used. As the light emitting group, a substance, such as a fluorescent pigment group as earlier referred to in the description of the device of the second aspect, can be used.

Also in the third aspect, the light emitting group may be added to the polynucleotide double strand by covalent bonding, or may be contained within the structure of the polynucleotide double strand (inserted between adjacent complementary moieties (intercalation)), or may be incorporated within a nucleotide chain by replacing a part thereof.

The electrode section used in the detecting unit of the device of the third aspect and the connection of the polynucleotide double strand thereto are as set out in the description of the detecting unit of the device of the first aspect.

In the device of the third aspect, the light emitting group is at the free end of the elongated polynucleotide double strand which is liable to fluctuate, so that it spontaneously fluctuates. Accordingly, in this device, the detection of protein is effected by the use of, for example, a phenomenon that the emission from the light emission group of the detecting section by the irradiation of exciting light fluctuates depending on the fluctuation of the polynucleotide double strand. The bonding of a protein to be detected to the bonding section leads to an increase in mass of the bonding section, and a slower fluctuation of the polynucleotide double strand of the detecting section compared to when the protein is not bonded. In consequence, the slower fluctuation is observed as slower fluctuation of the emission from the light emitting group and, using this, the bonding of the protein can be detected. By previously preparing a calibrated curve, quantitative determination of the protein is also possible.

More specifically, when the light emitting group is irradiated with exciting light, the electron of a light emitting group is excited, and fluorescence is observed when the excited electron goes back to an energy level lower than that at the excited state. On the other hand, the emission is prevented, and so-called quenching occurs, when the energy of the excited electron is lost outside the light emitting group due to, for example, overlap of electron orbits. If a substance for absorbing a positive or a negative charge is then provided outside the light emitting group, one of charges is lost from the light emitting group, resulting in charge separation (the development of charges). When all complementary base pairs are perfect in the polynucleotide double strand of the detecting section in the invention, the pi-electron orbits in the aromatic rings of adjacent bases forming the nucleotides overlap with each other, and form a so-called pi-electron stack to thereby exhibit electrical conductivity in the longitudinal direction of the strand. Migration of a high energy site or electric charge generated by the charge separation through the overlap of electron orbits makes the development of quenching easier. If the polynucleotide is then connected at one end to an electrode, the high energy site or electric charge lost from the light emitting group moves towards the electrodes as an electric current.

The polynucleotide double strand anchored to the electrode has natural fluctuation of structure due to thermal motion of molecules. When a crack (also called "nick") is introduced to one of the complementary two chains of polynucleotide, the fluctuation is enhanced, so that two conditions occur, the pi-electron stack being temporally broken up in one condition, and being restored in the other. Based on this, the movement of the high energy site or charge through the pi-electron stack is temporally prevented, which means that, with the molecular motion of polynucleotide, the loss and restoration of the quenching phenomenon are continuatively observed, and during which the intensity of emission varies corresponding to the motion (fluctuation) of the polynucleotide double strand. The fluctuation of the polynucleotide double strand is slow when the protein to be detected is bonded to the bonding section, and is fast when it is not bonded, as described above, so that it can be known, by the change in the intensity of emission, whether or not the protein is bonded to the bonding section.

FIG. 3A represents a graph schematically showing, as a function of time, the intensity of emission from a light emitting group and the amount of current running from the light emitting group to an electrode through a polynucleotide in the case where an objective protein is not bonded to the bonding section, and FIG. 3B represents a similar graph in the case where the objective protein is bonded to the bonding section. In the case where the protein is bonded, the bonding section has an increased mass, and the motion of the polynucleotide double strand will be slower compared to the case where the protein is not bonded. As a result, the time of quenching due to movement of the high energy site or electric charge through the pi-electron stack (during which the intensity of emission is lowered or not observed, and the high energy site or charge travels the pi-electron stack), and the time of emission during which the excited electron does not travel the pi-electron stack (and during which the intensity of emission is increased or observed), will be longer compared to the case where the protein is not bonded to the bonding section (the fluctuations of the intensity of emission and the current are mitigated).

As components other than the detecting unit composing the device of the third aspect of the invention, i.e., the container for sample solution, a unit for measuring emission, and a source of exciting light in the case of exciting the light emitting group by light, those commonly available can be used.

In the biopolymer detecting device of the invention, a member having a bonding site for detecting a biopolymer to be detected is used, the member being made up of a molecule having an affinity to the biopolymer, such as a protein, or a compound having interaction with the biopolymer to be detected. Representatives of the molecules or compounds are various proteins, including antibodies, RNAs, oligonucleotides and the like. It is also possible to use a complex of a combination of them as the member having the bonding site for detecting the biopolymer. By way of example, a complex of a combination of a protein and a nucleotide or a complex of a combination of an antibody and a nucleotide may be referred to.

The molecule or compound is fixed to an electrode of the detecting device of the invention. This can be effected by allowing a solution containing a certain molecule or compound to be contacted with the electrode for a predetermined time.

The molecule or compound may be fixed directly to the electrode (or a conductor layer of a stack, which is contacted directly with the sample solution, when the electrode incorporates a stack of layers of dielectric and conductor as described hereinafter), or may be fixed indirectly to the electrode through an appropriate ligand, such as thioether (—S—) group, or through a compound, such as a nucleotide. The fixing of the molecule or compound to the electrode (or the conductor layer) can be also effected using a material called a carbon nanotube or carbon nanofiber. The carbon nanotube or nanofiber can be formed by disposing a catalyst (made of, e.g., Ni or the like) on the electrode (or the conductor layer) to which the molecule or compound is to be fixed, and perpendicularly growing nanotubes or nanofibers from the surface of the electrode (or the conductor layer) by thermal CVD or plasma-enhanced CVD. A portion of the five-member rings at the end of the formed carbon nanotube or nanofiber can be readily chemically modified. Using this property, a certain molecule or compound can be joined to the end of the carbon nanotube or nanofiber. The carbon nanotube or nanofiber is a hard material, so that a molecule or compound bonded to the electrode (or the conductor layer) through such a material is more strongly fixed thereto, which is favorable for, for example, a case where a sample solution having a high viscosity is used (the fixed molecule or compound is subjected to a significant force when a high-viscosity solution is introduced to between the electrodes or is discharged after the measurement).

The electrode is made from a conductive material and, in general, a metallic material (for example, aluminum, copper or gold) can be used therefor. A pair of electrodes is arranged so as to sandwich therebetween a sample solution-holding section for holding a sample solution containing a biopolymer to be detected, to thereby form a type of capacitor. In this capacitor structure, at least one electrode can be formed so as to include a dielectric layer. When both electrodes are formed so as to include a dielectric layer, at least one electrode is configured so as to be indirectly contacted with a sample solution not through the dielectric layer but through the conductor layer. For example, when the electrode includes one dielectric layer, it is configured to have a stack structure of conductor layer/dielectric layer/conductor layer, and the member having the bonding site for detecting a biopolymer to be detected is fixed to the conductor layer which will be in contact with a sample solution. One electrode may contain a plurality of dielectric layers and, in this case, a conductor layer is interposed between adjacent dielectric layers. Using such an electrode including a dielectric layer or layers is useful to change a capacitance of a capacitor having a sample solution sandwiched between the electrodes thereof, to thereby change the sensitivity of a device. The dielectric layer may be formed using, for example, $SiO_2$, SiON, $Si_3N4$, carbon-based dielectric materials, tantalum oxide and the like. In the case of a stack structure containing a plurality of conductor layers, the conductor layers may be formed from the same material, or may be formed from different materials. Similarly, in the case of a stack structure containing a plurality of dielectric layers, they may be also formed from the same material, or they may be formed from different materials.

The biopolymer detecting device of the invention uses one or more pairs of capacitor electrodes to which a molecule having an affinity to a specific biopolymer, such as a protein, to be detected, or a compound having interaction with the biopolymer to be detected, and detects/determines the biopolymer present in a sample solution based on the change in signal resulted from the change in capacitance between the capacitor electrodes caused by the bond of the biopolymer to the electrodes. For the detection/determination, a calibration curve, prepared in advance, can be used. The detection and determination of the biopolymer to be detected are possible even when the detecting device has only one pair of electrodes. If two or more pairs of electrodes to which a molecule or compound useful for the detection of a biopolymer is fixed, a plurality of types of biopolymers present in a sample solution can be detected/determined together, based on the correspondence relationship between a signal developed by the bond of the biopolymer to the electrode and the location of the electrode developing the signal.

An electrical signal, as a signal that changes in accordance with the change in capacitance between the capacitor electrodes, caused by the bond of the biopolymer to be detected to the electrode, is processed by an electric circuit contained in a detecting device. Specifically, the electrical signal is detected, herein, as the change in the amount of electric charge (interelectrode capacitance) accumulated between the electrodes, or as the difference in current passing between an electrode of one pair of electrodes having the site capable of being bonded to the biopolymer to be detected and an electrode of another pair of reference electrodes, as a result of the difference in the amount of accumulated charge between one pair of electrodes and another pair of electrodes. For example, the change in electric charge is measured by a coulometer, and the current is measured by an ammeter. Alternatively, the measurement may be effected using a transistor, a device using an MIS structure, a device using a p-n junction, a device having a Schottky junction, or a combination thereof. Such a measuring means may be included in the detecting device of the invention, or may be set up outside the device. The electric circuit for processing electrical signals in the detecting device of the invention is constructed so as to contain such a measuring means in the former case, and is designated for the connection (electrical connection) with an external measuring instrument in the latter case, with the measurement itself being externally carried out (in this case, the processing in the electric circuit of the detecting device represents the transmission of the electric signal to the exterior).

The biopolymer detecting device of the invention can be provided with terminals (lead electrodes) for connecting its electric circuit to an external electrical circuit. In the case of the device in which the change in the amount of electric charge accumulated between the electrodes is measured, the device having only one terminal of the simplest embodiment makes in possible to carry out the measurement by an external ammeter which is grounded.

The device of the invention needs to have a sample solution-holding section for holding a sample solution containing a biopolymer between the electrodes during the measurement. The sample-solution holding section may be a gap portion between the electrodes of a capacitor structure. Fluid channels, such as those for feeding a sample solution to the holding section and for discharging the sample solution from the holding section, may be connected to the holding section.

Preferably, the devices of the invention are fabricated in the same substrate utilizing the techniques of photolithography and film formation used in the manufacture of semiconductor devices and the like. As the substrate, a substrate of silicon or sapphire can be used.

The biopolymer detecting device according to the invention represents a so-called protein chip, and is designed to detect, for example, the decline or enhance of part of a series of protein interaction network function starting from insulin receptor and ending with glycogen catabolic enzyme in the case where hepatocyte having diabetes switches the intracellular metabolism of glycogen depending on a state of insulin acceptance. By the use of this technique, it becomes possible to know the population of proteins, including a so-called posttranslational modification such as a phosphorylation or an addition of a sugar chain. Consequently, instead of detecting diabetes mellitus on the basis of symptom as before, it becomes possible to know that the decline in function of a certain protein pertaining to the interaction network causes incompetence of glucose metabolism, and appropriate diagnosis and cure corresponding to the cause of disfunction, as well as verification of a therapeutic result, become possible.

Of course, a similar technique can be applied to the entirety of multifactorial disease, such as hypertension, hyperlipidemia or the like, in addition to diabetes mellitus.

EXAMPLES

The invention will now be described referring to the following examples, although the invention is not to limited to these examples.

Example 1

Figure 4:
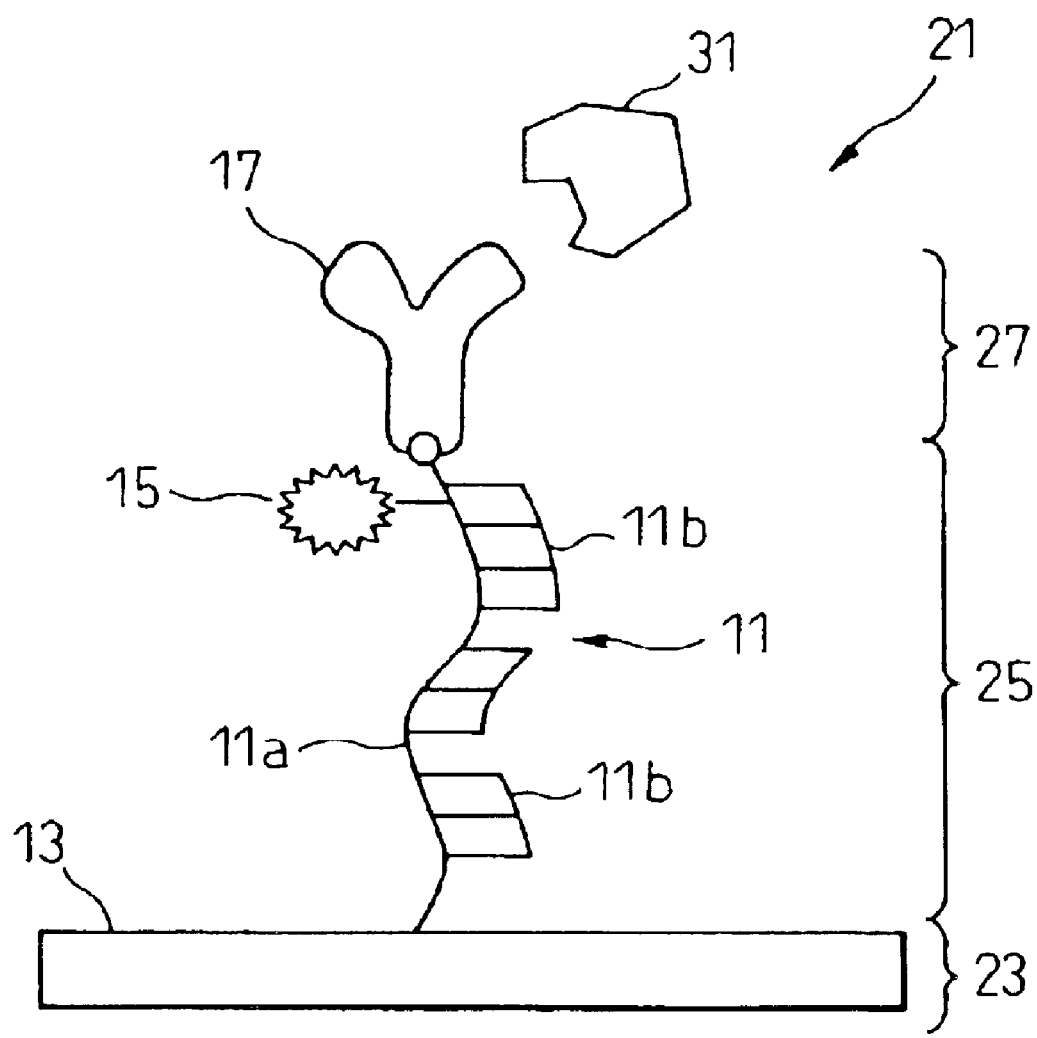

As schematically shown in FIG. 4, a one-chain polynucleotide 11a, to one end of which a mercapto group was introduced through a spacer, was synthesized, and was hybridized with a complementary one-chain polynucleotide 11b, which was similarly synthesized, to form a polynucleotide double strand structure 11, which was then reacted with a polished gold electrode 13 at room temperature for 24 hours to be bonded to the gold electrode 13.

Using a solution in which iron porphyrin, as a charge separating group 15 causing charge separation, was dissolved, the charge separating group 15 was absorbed to (intercalated in) the pi-electron stack of the polynucleotide double strand structure 11 on the gold electrode 13. Alternatively, a group derived from such a charge separating group may be covalent-bonded to the polynucleotide chain, or part of a nucleotide base may be substituted with a group derived from such a pigment. Subsequently, a Fab fragment 17 of a monoclonal immunoglobulin IgG was fixed to the end of the polynucleotide chain.

As shown in FIG. 4, a detecting unit 21 thus fabricated was formed of an electrode section 23, a detecting section 25, and a bonding section 27. The antibody 17 of the bonding section 27 is specifically bonded only to a particular protein 31 to be detected.

The electrode 13 is, in general, positioned on a support which is not shown. By arranging, in a single detecting unit, a plurality of electrodes 13 in the form of an array, and bonding different antibodies to the bonding sections corresponding to different electrodes, it becomes possible to detect/determine a plurality of proteins by the single detecting unit.

The detecting unit 21 as fabricated above was immersed in an aqueous solution containing ferrocyanide ion as a charge acceptor, and a current running through the polynucleotide double strand structure 11 was measured by a three-electrode method using a reference electrode (not shown). Subsequently, using an aqueous solution containing a protein to be detected in addition to the charge acceptor, a similar measurement was performed.

The conductivity developed by the polynucleotide double strand in the longitudinal direction of the strand by the pi-electron stack of the aromatic rings of bases composing the nucleotides was lost in a condition that the stack of pi-electron was temporarily broken up by molecular motion of the double strand structure. It was observed that the temporary loss of conductivity was made preeminent particularly by purposely introducing a crack or cracks in the double strand, as shown in FIG. 4.

In addition, when a solution containing no proteins was used for the measurement, no differences were observed in appearance of the loss and restoration of the conductivity measured for the respective gold electrodes. In contrast, when the solution containing proteins was used, it was observed that the loss and restoration of the conductivity was slow for the electrodes corresponding to the bonding sections to which the protein was bonded, and patterns of the loss and restoration of the conductivity observed for those gold electrodes were different from each other corresponding to the molecular weights of the bonded proteins. Fluctuation of the conductivity occurred at a high frequency for the nucleotide chain to which no protein was bonded, and the fluctuation was mitigated when a protein was bonded to the nucleotide chain to increase the mass thereof, the mitigation of the fluctuation being more enhanced as the mass of the protein bonded became larger.

Thus, in the invention, the determination of a protein to be detected can be made by detecting a phenomenon of the fluctuation of conductivity developed by a polynucleotide double strand being mitigated by the protein bonded thereto. By the use of a plurality of electrodes, and the use of different antibodies for different bonding sections corresponding the electrodes, it also becomes possible to identify and detect unknown kinds of protein.

The sensitivity for detecting a protein is varied depending on the molecular weight of a protein bonded to the bonding section, and is also varied depending on a bonding constant of the protein with a monoclonal IgG antibody. Accordingly, by the use of a plurality of measuring electrodes for the same protein, and providing, corresponding to the respective electrodes, bonding sections of monoclonal antibodies having bonding constants for the protein which are different from each other, measurement can be performed over a wide range of the concentration of protein.

Figure 5:
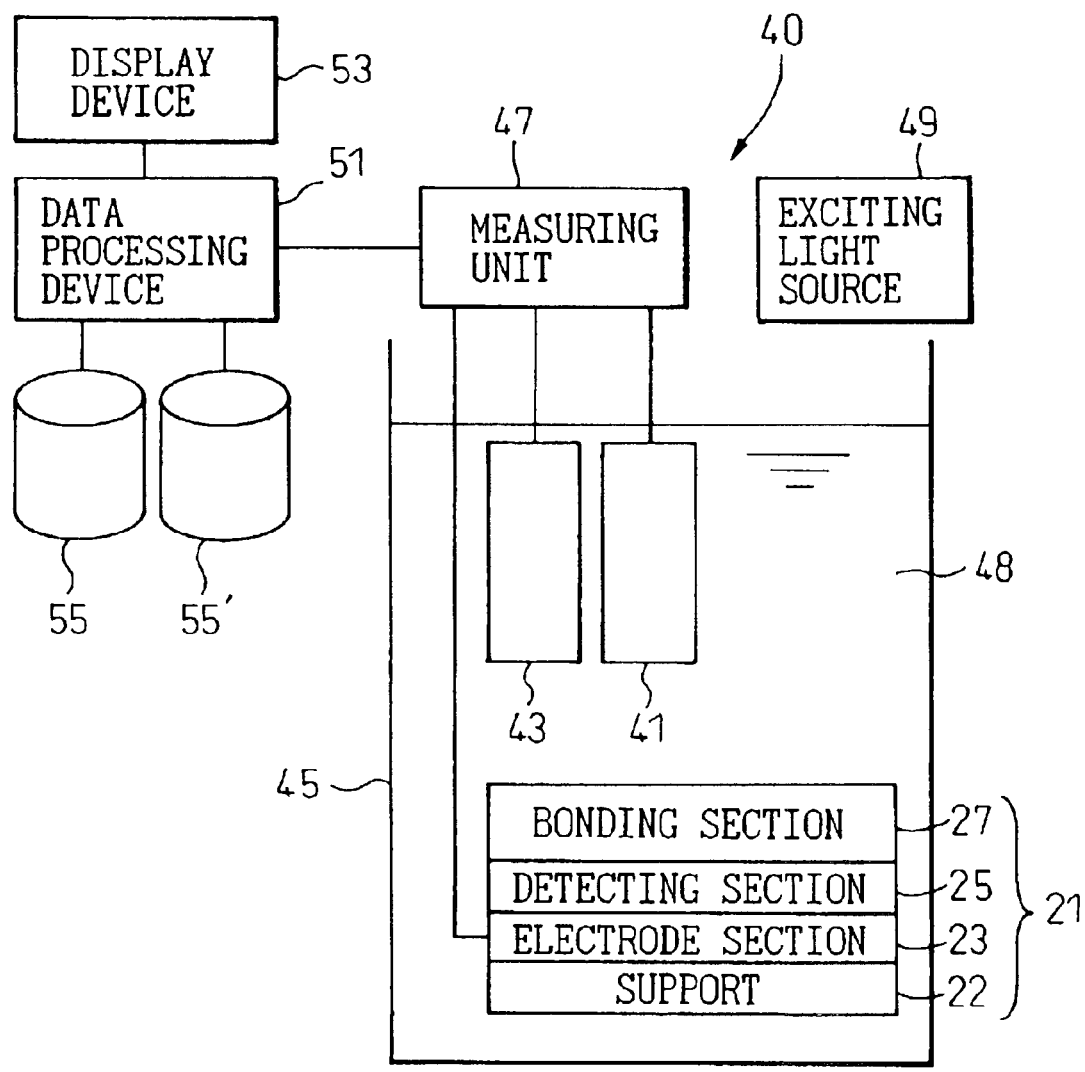

The entire construction of a measuring apparatus using the protein detecting device illustrated in this example is schematically shown in FIG. 5. The measuring apparatus shown in the drawing uses a protein detecting device 40 comprising a sample container 45 which contains a detecting unit 21 made up of a support 22, the electrode section 23, the detecting section 25 and bonding section 27, a standard electrode 41, and a standard electrode 43, and further including a measuring unit 47 which is connected to the respective electrodes 23, 41, 43. A sample solution 48 containing a protein to be detected is added to the sample container 45. If the detecting section 25 is of a type of charge separating group generating an electron and an positive hole upon light excitation, there is provided an exciting light source 49. The measuring unit 47 of the protein detecting device 40 is preferably connected to a data processing device 51 for processing measured data, the data processing device 51 being accompanied with a device 53 for displaying measured results and a memory storage or storages 55, 55' for storing the arrangement of an array, calibrated values for the detecting unit 21 and the like.

Example 2

A one-chain polynucleotide, to the 5' end of which a mercapto group was introduced through a spacer, was synthesized, and was hybridized with a one-chain polynucleotide, which had a complementary sequence and the 5' end to which a fluorescent pigment (Cy3 (trade mark)) was introduced, to form a polynucleotide double strand structure, which was then reacted with a polished gold electrode positioned on a support at room temperature for 24 hours to be bonded to the gold electrode. It is preferable that the degree of polymerization of the polynucleotide chain is such that it has 12 to 100 monomer residues. The mercapto group and the fluorescent pigment may be introduced to the ends of one of the one-chain polynucleotides, respectively, or may be introduced to the 3' ends of both the one-chain polynucleotides.

The polynucleotide double strand structures were fixed in a circular area of 10 micrometers, around which a spacer area having no polynucleotide double strands fixed was provided. As a quenching pigment providing effective quenching for the fluorescent pigment introduced to the polynucleotide chain, Cy5 (trade mark) was fixed onto the surface of the gold electrode. In addition, a Fab fragment of monoclonal immunoglobulin IgG was fixed to the end of the polynucleotide chain. Herein, Fab fragments which were different in specificity were fixed to the respective groups of polynucleotides separated from each other by the spacer area.

Figure 6:
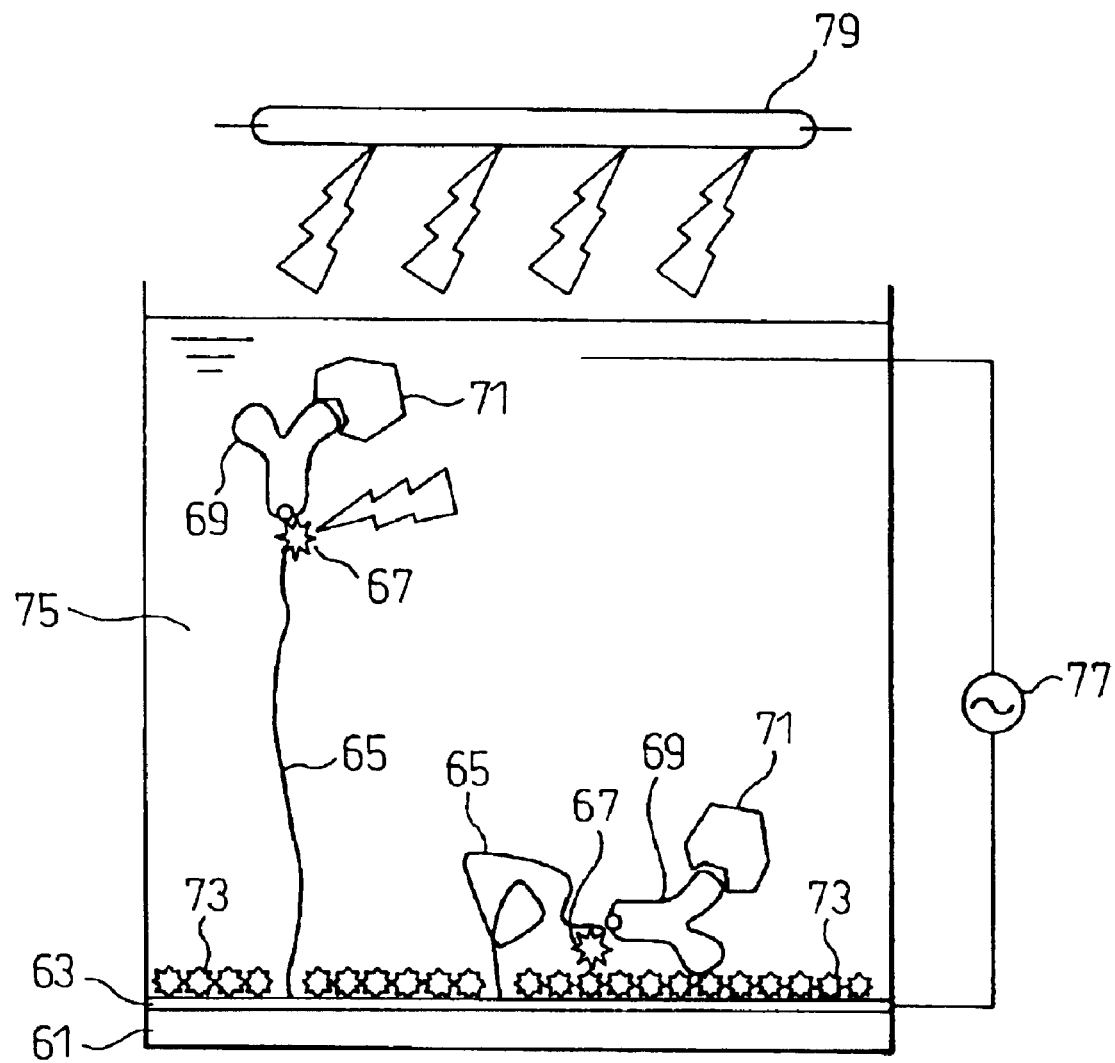

The detecting unit thus fabricated is schematically shown in FIG. 6. The support, gold electrode, polynucleotide double strand (which is depicted by a single line for simplification), fluorescent pigment, Fab fragment, protein, and quenching pigment are identified by reference numerals 61, 63, 65, 67, 69, 71, and 73, respectively.

The detecting unit was then put into contact with a sample solution containing a protein to be detected, and was allowed to stand at room temperature for a sufficient time to form a bond of the Fab fragment 69 and the protein 71, as shown in FIG. 6.

The detecting unit having the protein thus bonded was immersed in an aqueous solution, as also shown in FIG. 6, and an AC field was applied to the polynucleotide double strand structures 65 by a two-electrode method (alternatively, a three-electrode method may be used) using a AC power supply 77, waiting until the fluorescent pigment 67 on the polynucleotide double strand was excited by a UV lamp 79 to generate fluorescence and the intensity of fluorescence became steady. Subsequently, the AC field was removed, and after the establishment of a steady state, rates of decrease in the intensity of fluorescence were measured for the respective groups of polynucleotide double strand structure.

The left polynucleotide double strand structure 65 schematically depicted in FIG. 6 represents one at an electric field applied state, and the right double strand structure 65 represents one at a no electric field state (no electric filed applied state). For the double strand structure 65, having been linearly elongated at the electric field applied state, the polynucleotide double strand is spontaneously flocculated upon disappearance of the electric field, and the fluorescent pigment 67 at the end of the double strand structure 65 comes close to the quenching pigment 73 on the surface of the gold electrode, as shown in the right side of FIG. 6, whereby a decrease in the intensity of fluorescence is observed.

When the protein to be detected present in the sample solution is bonded to the Fab fragment, the mass at the end of the polynucleotide double strand is increased, resulting in the increase in time taken for the spontaneous flocculation, i.e., time taken for the decrease in the intensity of fluorescent. The extent by which the time is increased is varied depending on the amount of protein present in the sample solution, so that, by knowing the extent, the amount of protein in the sample solution can be measured, and the type of protein can be identified depending on what polynucleotide strand the signal comes from.

Also, in this example, the sensitivity for detecting a protein is varied depending on the molecular weight of a protein bonded to the bonding section, and is also varied depending on a bonding constant of the protein with a monoclonal antibody. Accordingly, by arranging, in the form of an array, several sensing sections using monoclonal antibodies having different bonding constants for the same protein, measurement can be performed over a wide range of the concentration of protein.

The entire construction of a measuring apparatus using the protein detecting device illustrated in this example is schematically shown in FIG. 7. The measuring apparatus shown in the drawing uses a protein detecting device 110 comprising a detecting unit 92 made up of a support 80, a gold electrode 82, which is one electrode of a controlling section, a detecting section 84 of a quenching pigment, a sensing section 86 of polynucleotide double strand structures and a fluorescent pigment, a bonding section 88 of a Fab fragment and another electrode 90 of the controlling section, and a sample container 94 in which the detecting unit 92 is contained, and further including a power supply 96 connected to the respective electrodes 82, 90, an exciting light source 98, and a fluorescence measuring unit 100. A sample solution 102 containing a protein to be detected is added in the sample container 94. The measuring unit 100 of the protein detecting device 110 is preferably connected to a data processing device 122 for processing measured data, the data processing device 122 being accompanied with a device 124 for displaying measured results and a memory storage or storages 126, 126' for storing the arrangement of an array, calibrated values for the detecting unit 92 and the like.

Example 3

A detecting unit was fabricated as in Example 1, except that Cy3 or FITC was used as an light emitting group in place of the charge separating group used in Example 1.

A one-chain polynucleotide, to one end of which a mercapto group was introduced through a spacer, was synthesized and was hybridized with a complementary one-chain polynucleotide 11b, which was similarly synthesized, to form a polynucleotide double strand structure, which was then reacted with a polished gold electrode at room temperature for 24 hours to be bonded to the gold electrode.

Using a solution in which a light emitting group was dissolved, the light emitting group was intercalated in the pi-electron stack of the polynucleotide double strand on the gold electrode. Alternatively, a nucleotide base may be replaced by a derivative of the light emitting group. Subsequently, a Fab fragment of a monoclonal immunoglobulin IgG was fixed to the end of the polynucleotide chain.

A detecting unit thus fabricated was as shown in FIG. 4, and was similar to the detecting unit fabricated in Example 1, except that iron porphyrin was used as a charge separating group 15 in Example 1, whereas the Cy3 was used herein as the light emitting group 15. Thus, the detecting unit 21 in this example was also formed of an electrode section 23, a detecting section 25, and a bonding section 27. Also, the antibody 17 of the bonding section 27 is specifically bonded only to a particular protein 31 to be detected.

The fabricated detecting unit 21 (FIG. 4) was immersed in a sample solution containing no protein to be detected, and was irradiated with exciting light to make the light emitting group emit light. It was confirmed that the intensity of emission was significantly increased in the condition that the electrical conductivity of the pi-electron stack of the polynucleotide double strand was temporally lost by molecular motion (fluctuation of the intensity of emission was observed). In addition, in a detecting unit in which a crack was purposely introduced in the polynucleotide double strand, it was observed that the fluctuation of the intensity of emission was more significant.

Subsequently, the detecting unit was immersed in a sample solution containing a protein 31 (FIG. 4) to be detected, and was allowed to stand at room temperature for a sufficient time for the protein 31 to be bonded to the Fab fragment 17, after which a similar experiment was carried out by irradiating the detecting unit with exciting light. In this case, the fluctuation of the intensity of emission was slower compared to the case where the protein was not bonded, due to the increase in mass in the bonding section of the detecting unit by the bond of the protein thereto.

Thus, the detection of a protein to be detected becomes possible by detecting a phenomenon of the fluctuation of conductivity developed by a polynucleotide double strand being mitigated by the protein bonded thereto, as the fluctuation of the intensity of emission from the light emitting group added to the polynucleotide double strand. In addition, use of a calibration curve makes the determination of the protein possible.

Sensitivity for detecting a protein is varied depending on the molecular weight of a protein bonded to the bonding section, and is also varied depending on a bonding constant of the protein with a monoclonal IgG antibody. Thus, by the use of a plurality of measuring electrodes for the same protein, and providing, corresponding to the respective electrodes, bonding sections of monoclonal antibodies having bonding constants for the protein which are different from each other, measurement can be performed over a wide range of the concentration of protein.

The entire construction of a measuring apparatus using the protein detecting device illustrated in this example is schematically shown in FIG. 8. The measuring apparatus shown in the drawing uses a protein detecting device 200 comprising a detecting unit 21 made up of a support 22, an electrode section 23, a detecting section 25 and a bonding section 27, a sample container 201 in which the detecting unit 21 is contained, an exciting light source 202, and a measuring unit 203. A sample solution 204 containing a protein to be detected is added in the sample container 201. The measuring unit 203 of the protein detecting device 200 is preferably connected to a data processing device 211 for processing measured data, the data processing device 211 being accompanied by a device 212 for displaying measured results and a memory storage or storages 213, 213' for storing the arrangement of an array, calibrated values for the detecting unit 21 and the like. If a light emitting group, which emits light upon the application of bias, is used, the exciting light source 202 can be omitted.

In this apparatus, the electrode section 23 of the detecting unit 21 is connected to the measuring unit 203. In the case where a light emitting group of a type of emitting light upon the application of bias is used in place of the light emitting group emitting upon the irradiation with exciting light used in this example, it is possible to apply bias to the light emitting group through the electrode section 23. When the current running from the light emitting group to the electrode section 23 through the polynucleotide double strand is to be detected, in addition to the intensity of emission, the measuring unit 203 can include an ammeter (not shown) to thereby carry out the current measurement.

Example 4

This example describes the production of a biopolymer detecting device.

Figure 9A:
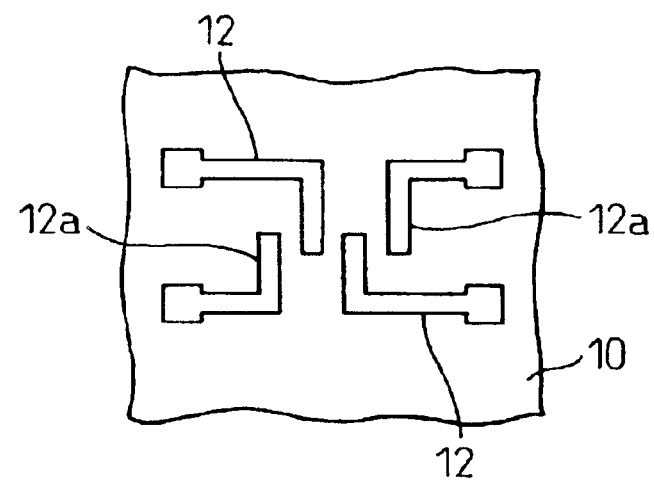
FIGS. 9A to 9G illustrate the process for manufacturing the biopolymer detecting device described in Example 4.

As shown in FIG. 9A, a metallic layer made up of films of Ti, Pt, Au, Pt and Ti formed, in this order, on a silicon substrate 10 was patterned to form wiring lines 12. Of the drawings referred to in this example, only FIG. 9A is a top view, and the others are shown in cross-sections. In addition, the wiring lines 12 are depicted only in FIG. 9A, for simplicity. Also, although a number of devices were simultaneously fabricated on a common silicon substrate, the drawings (FIGS. 9 and 10) associated with this example illustrate only a single sample solution-holding section and the vicinity thereof, for simplicity.

Figure 9B:
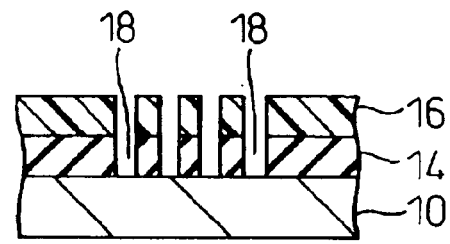
Figure 9C:
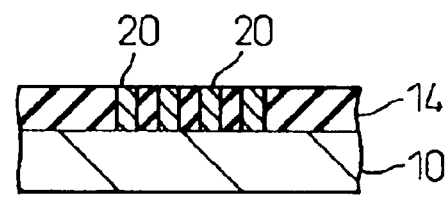

As shown in FIG. 9B, an $SiO_2$ film 14 (1 micrometer thick) was formed on the surface of the silicon substrate 10 having the wiring lines formed, and was patterned by dry etching using a resist pattern 16 formed thereon as a mask, to create trenches 18. Subsequently, an Au film (not shown) was formed on the entire surface of the substrate, and the resist pattern 16 and the Au film thereon were removed by a lift-off process, to thereby fill the trenches 18 (FIG. 9B) in the $SiO_2$ film 14 with Au conductor 20, as shown in FIG. 9C. The Au conductor 20 was designed to be located on one end 12a (FIG. 9A) of the wiring line 12 on the silicon substrate 10, although the wiring lines 12 are not shown in FIG. 9B and the following drawings.

Figure 9D:
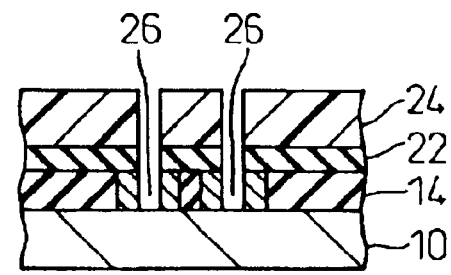
Figure 9E:
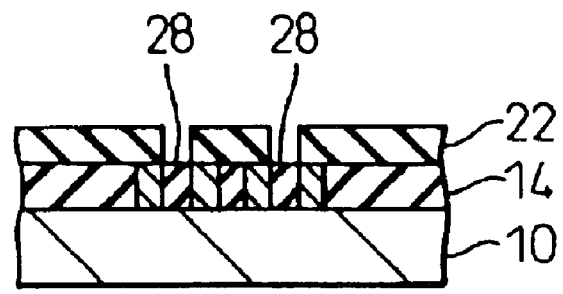

As shown in FIG. 9D, an additional $SiO_2$ film 22 (1 micrometer thick) was then formed on the $SiO_2$ film 14, and the $SiO_2$ films 22 and 14 were successively dry etched using a resist pattern 24 formed on the additional $SiO_2$ film 22 as a mask, to thereby form trenches 26. Subsequently, an $Si_3N_4$ film (not shown) was formed on the entire surface of the substrate, and the resist pattern 24 and the $Si_3N_4$ film thereon were removed by a lift-off process, to thereby fill the trenches 26 (FIG. 9D) with $Si_3N_4$ dielectric 28, as shown in FIG. 9E. The $Si_3N_4$ dielectric 28 thus filled had a height approximately equivalent to a thickness of the underlayer of $SiO_2$ film 14.

Figure 9F:
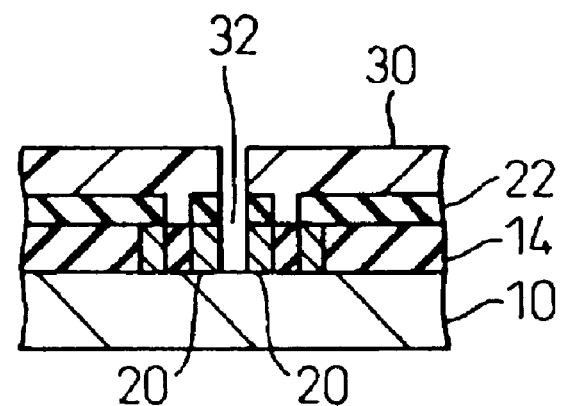

Subsequently, as shown in FIG. 9F, a resist pattern 30 was formed so as to cover the upper layer of $SiO_2$ film 22, and was used as a mask for successive dry etching of the $SiO_2$ films 22 and 14, to thereby form a trench 32, which serves as a sample solution-holding section of a device, and at both sides of which the Au conductor 20 was exposed.

Figure 9G:
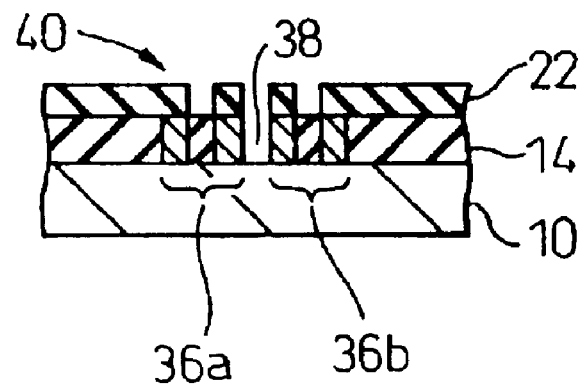

After peeling the resist pattern 30, the trench 32 was filled with a solution containing an oligonucleotide, and the oligonucleotide (not shown) was reacted with the Au conductor 20 at room temperature for 24 hours to be bonded thereto, and to provide a biopolymer detecting device 40 comprising a sample solution-holding section 38 sandwiched by capacitors 36a and 36b, as shown in FIG. 9G.

Figure 10:
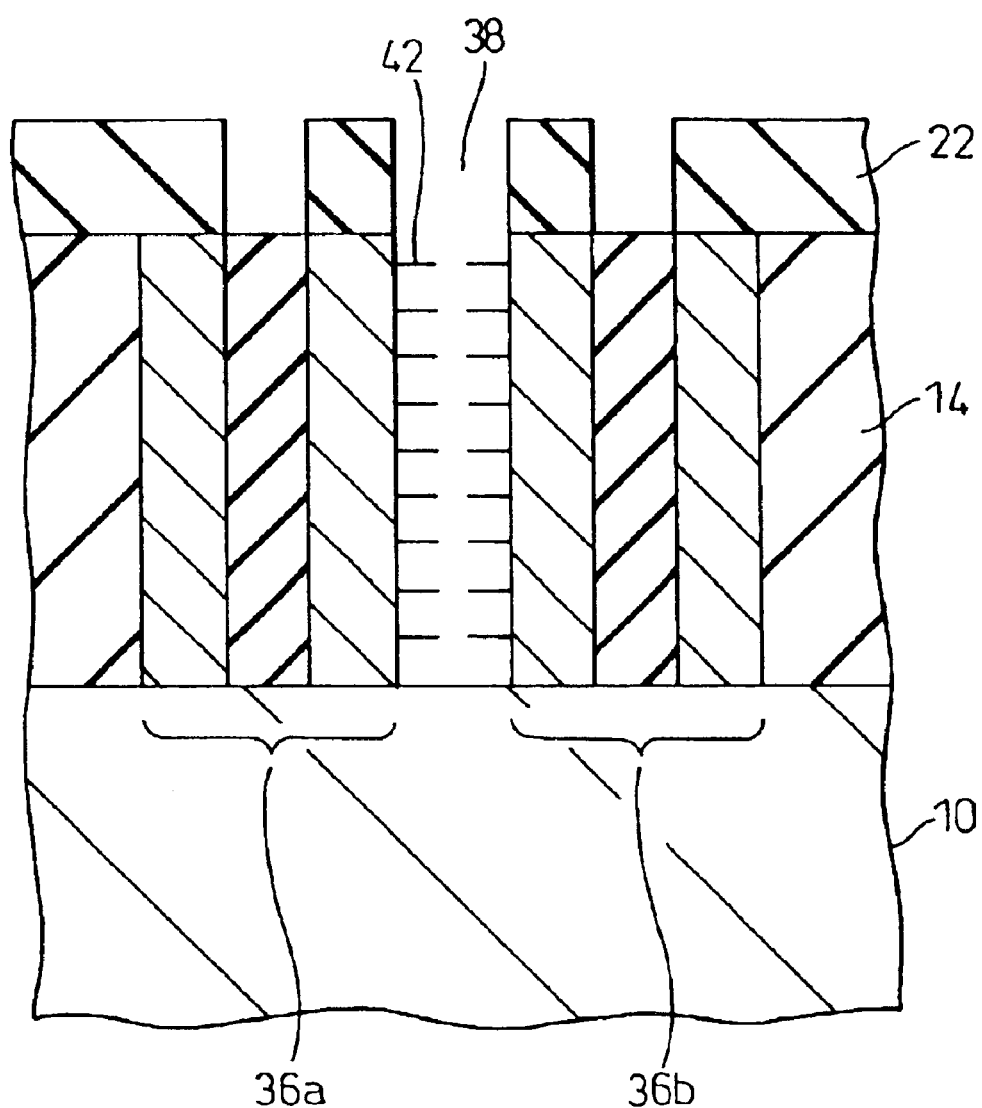
FIG. 10 is an schematically enlarged section of the sample solution-holding section of the biopolymer detecting device manufactured in Example 4.

Portion of the sample solution-holding section 38 of the device is enlarged and shown in FIG. 10. A number of oligonucleotides 42 are bonded at one end to the surface of the Au conductor exposed at both sides of the sample solution-holding section 38.

Example 5

Figure 11:
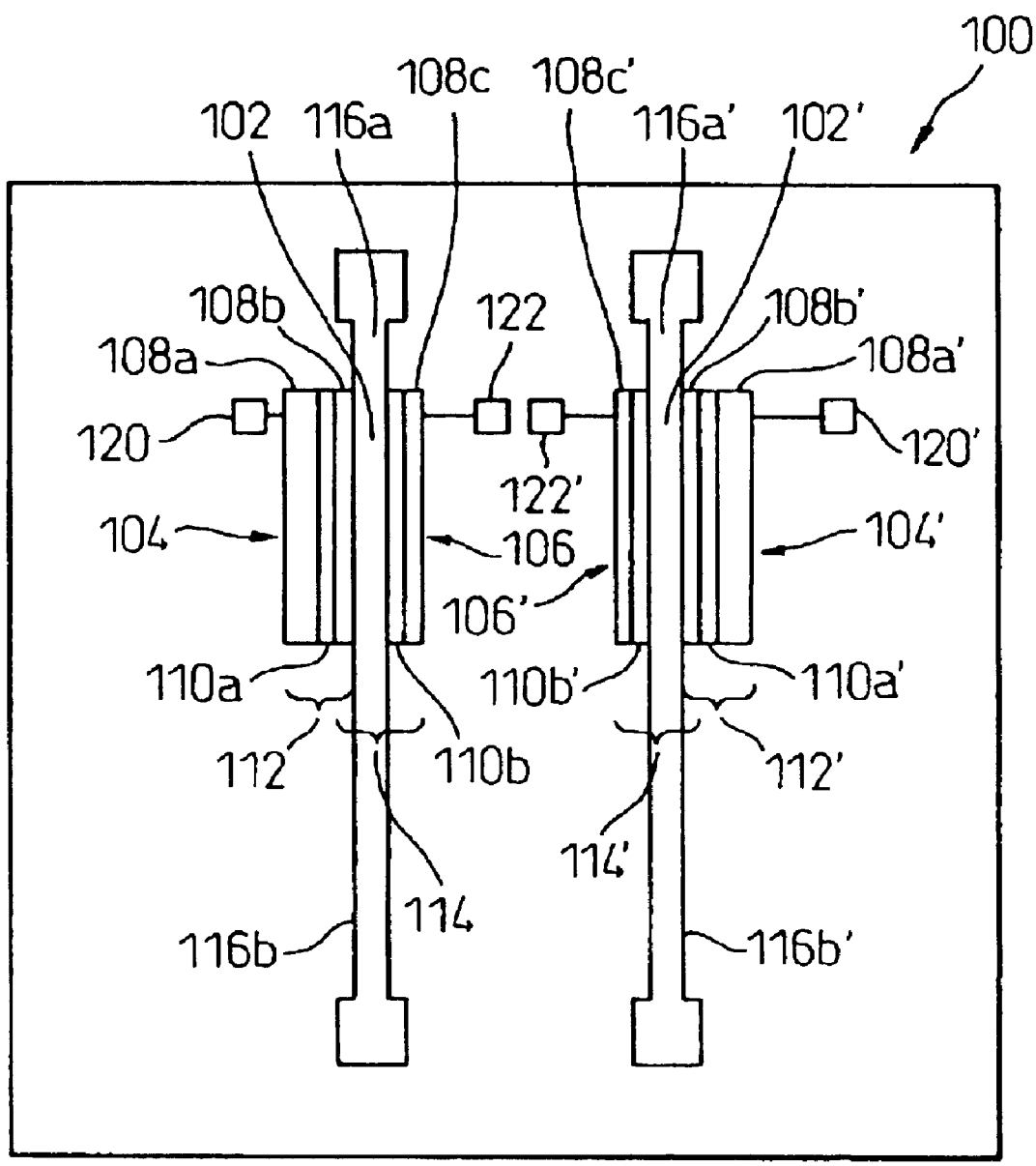
FIG. 11 illustrates the biopolymer detecting device of Example 5.

Following the procedure described in Example 4, a biopolymer detecting device 100, as shown in FIG. 11, was made. In the device described in Example 4, the electrodes at both sides of the sample solution-holding section had a capacitor structure made up of the two Au films and the $Si_3N_4$ dielectric film therebetween, whereas in the device 100 of this example having two sample solution-holding sections 102, 102', an electrode 104 (104') at one side of each of the sample solution-holding sections 102, 102' forms a capacitor 112 (112') made up of two Au conductor layer 108a and 108b (108a', and 108b') and an $Si_3N_4$ dielectric layer 110a (110a') interposed therebetween, and an electrode 106 (106') opposed to the electrode 104 (104') and sandwiching the sample solution-holding section therebetween is made up of an Au conductor layer 108c (108c') and an $Si_3N_4$ dielectric layer 110b (110b'), and forms a capacitor 114 (114'), which is connected in series to the capacitor 112 (112'), together with the Au conductor layer 108b (108b'), which is opposed to the layer 110b (110b') and sandwiches the sample solution-holding section 102 (102') therebetween. For the connection with an external circuit, lead electrodes 120, 122, 120', 122' connected to the respective electrodes 104, 106, 104', 106' were provided.

Antibodies 132 were bonded to the Au conductor layers 108b, 108b' exposed at the sample solution-holding sections 102, 102' by filling the sample solution-holding sections 102, 102' with an antibody containing solution and allowing it to stand at room temperature for 24 hours. To facilitate the filling of the sample solution-holding section 102, 102' with the antibody-containing solution and a sample solution to be measured, the device 100 of this example is provided with fluid channels 116a, 116b, 116a', 116b', communicating with the sample solution-holding sections 102, 102'. Using the fluid channels, the sample solution-holding sections 102, 102' can not only be filled with a solution, but also allow the solution to pass therethrough. The sample solution-holding section had a length and a width of about 1 millimeter and about 1 micrometer, respectively.

Figure 12:
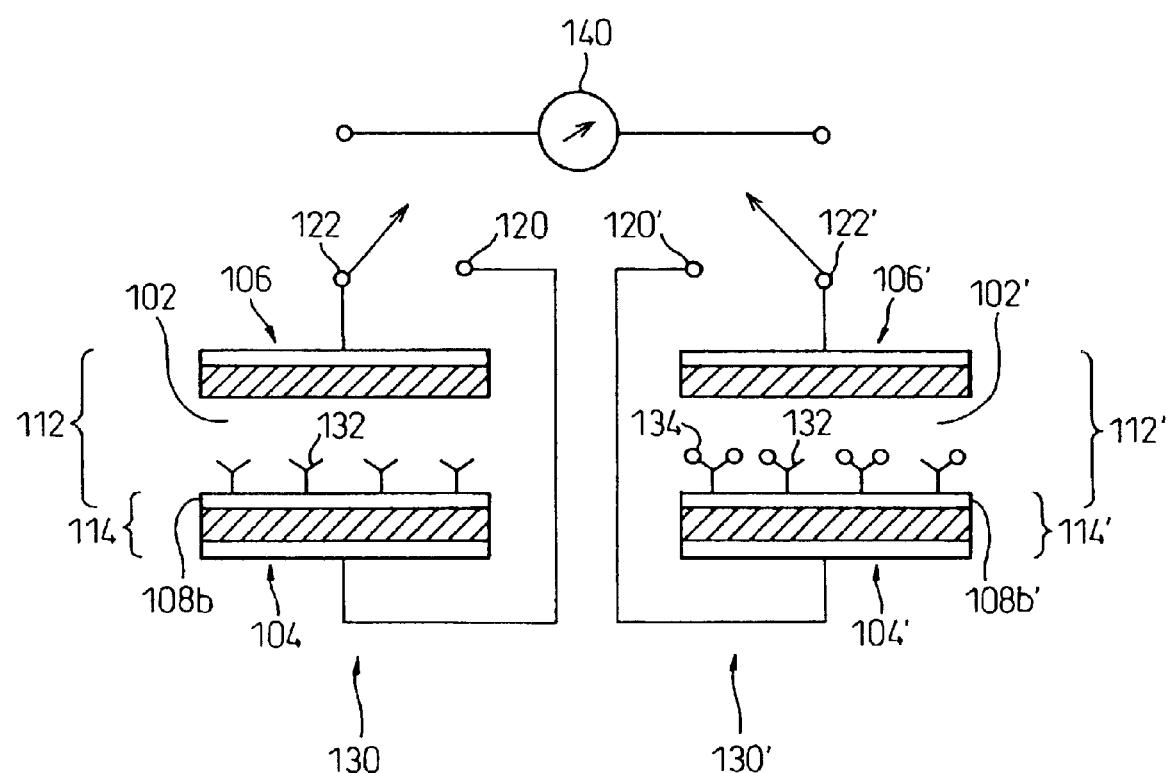
FIG. 12 illustrates the measuring system used in Example 5.

The measuring system used in this example is schematically shown in FIG. 12. In the drawing, a detecting system 130 for the sample solution-holding section 102 is shown at the left side, and a detecting system 130' for the sample solution-holding section 102' is shown at the right side, corresponding to the device shown in FIG. 11. Prior to the initiation of measurement, antibodies 132 were bonded to the Au conductor layers 108b, 108b' exposed at the sample solution-holding sections 102, 102'.

The capacitors 112 and 112' were allowed to accumulate electric charge by applying a DC bias to between the electrodes 104 and 106 and the electrodes 104' and 106' of the detecting systems 130 and 130', respectively, using a DC bias source (not shown). The circuit for applying the bias was then disconnected, and a current passing between the lead electrodes 122 and 122', when there was a difference between the electrical charges accumulated in the respective electrodes 106 and 106', was measured using a galvanometer 140, as follows.

A sample containing no protein bonding to the antibody 132 was passed from the fluid channels 116a, 116a' (FIG. 11) to the sample solution-holding sections 102, 102', and an equivalent value of DC bias was applied to between the lead electrodes 120 and 122 and the lead electrodes 120' and 122', after which the circuit for applying the bias was disconnected. The galvanometer 140 was connected to between the lead electrodes 122 and 122' to measure a current passing between the lead electrodes 122 and 122', and it was confirmed that no current was detected.

Next, a sample containing a protein bonding to the antibody 132 was passed through the sample solution-holding section 102, 102', and an equivalent value of DC bias was applied to the lead electrodes 120 and 122 and the lead electrodes 120' and 122', after which the circuit for applying the bias was disconnected. The galvanometer 140 was connected to between the lead electrodes 122 and 122' to measure a current passing between the lead electrodes 122 and 122', and it was confirmed that no current was detected.

Subsequently, the sample containing no protein bonding to the antibody 132 was passed through the sample solution-holding section 102 of the detecting system 130, the sample containing the protein 134 bonding to the antibody 132 (the conditions of solvent for this sample were the same as those for the sample containing no protein) was passed through the sample solution-holding section 102' of the detecting system 130', and an equivalent value of DC bias was applied to between the lead electrodes 120 and 122 and the lead electrodes 120' and 122', after which the circuit for applying the bias was disconnected. When the galvanometer 140 was connected to between the lead electrodes 122 and 122' to measure a current passing between the lead electrodes 122 and 122', a current could be detected.

Similar measurements were carried out using samples having various concentrations of protein 134 bonding to the antibody, and a calibration curve of the protein concentration relative to the current value was obtained by plotting the protein concentrations and the current values measured.

FIG. 6 shows a flow chart indicating the procedure when the determination of a protein to be detected is carried out using a calibration curve.

As described, the invention makes it possible to specifically and conveniently detect/determine a biopolymer, such as a protein, without labeling the biopolymer itself with, for example, fluorescence. By implementing the invention as a device in which multiple pairs of electrodes are arranged on the same substrate in the form of an array, it is also possible to apply the invention to proteome analysis in which biopolymers are assessed as a mass.

What is claimed is:

1. A protein detecting device, which comprises:
   (1) a detecting unit having a bonding section, which has properties for specifically bonding to a protein to be detected, a detecting section for detecting the bording of the protein to be detected to the bonding section, the detecting section being made up of a polynucleotide double strand and a charge separating group, and an electrode section picking up the change in electrical conductivity of or amount of transferred charge in the polynucleotide double strand modified by the bond of the protein,
   (2) a standard electrode,
   (3) a reference electrode,
   (4) a container for housing the detecting unit, the standard electrode and the reference electrode, and containing a sample solutions comprising the protein to be detected, and
   (5) a measuring unit for measuring the protein based on a signal detected in the detecting unit;
   wherein:
   one end of said polynucleotide double strand is connected to said electrode section; and
   the other end of said polynucleotide double strand is connected to said bonding section.

2. The protein detecting device of claim 1, wherein the charge separating group is added to the polynucleotide double strand by covalent bonding, or is interposed in the structure of the polynucleotide double strand, or is incorporated within a nucleotide chain forming the polynucleotide double strand by replacing a part thereof.

3. The protein detecting device of claim 1, wherein the charge separating group is present in the vicinity of the end of the polynucleotide double strand structure at the side of the bonding section.

4. The protein detecting device of claim 1, wherein the bonding section is formed of a substance selected from the group consisting of antibodies which specifically bond to the protein to be detected or fragments of the antibodies, and organic compounds and biopolymers having an affinity to the protein to be detected.

5. The protein detecting device of claim 4, wherein the substance forming the bonding section is fixed to the polynucleotide double strand of the detecting section by directly connecting it to the polynucleotide double strand.

6. The protein detecting device of claim 4, wherein the substance forming the bonding section is connected to the polynucleotide double strand of the detecting section through a connecting moiety useful to connect and fix the substance to the polynuQleotide double strand.

7. The protein detecting device of claim 1, wherein the bonding section is formed of an IgG antibody.

8. The protein detecting device of claim 1, wherein the bonding section is formed of a monoclonal immunoglobulin IgG antibody.

9. The protein detecting device of claim 1, wherein the bonding section is formed of a Fab fragment of a monoclonal immunoglobulin IgG antibody or a piece derived from the Fab fragment.

10. The protein detecting device of claim 1, wherein one of the polynucleotide chains of the polynucleotide double strand has a discontinuity at one or more locations along the chain.

11. The protein detecting device of claim 1, wherein the change in electrical conductivity of or amount of transferred charge in the polynucleotide double strand of the detecting section is detected by the modification of the pi-electron stack in the polynucleotide double strand caused by the molecular motion of the double strand.

* * * * *